(12) United States Patent
Dong et al.

(10) Patent No.: US 11,821,885 B2
(45) Date of Patent: Nov. 21, 2023

(54) TEST METHODS FOR SIMULATING SEDIMENT POLLUTANT RELEASE UNDER EFFECT OF RIVER CHANNEL EROSION

(71) Applicants: TIANJIN PORT ENGINEERING INSTITUTE CO., LTD. OF CCCC FIRST HARBOR ENGINEERING CO., LTD., Tianjin (CN); CCCC FIRST HARBOR ENGINEERING CO., LTD., Tianjin (CN); TIANJIN PORT ENGINEERING QUALITY TESTING CENTER CO., LTD., Tianjin (CN); CHANGJIANG WUHAN WATERWAY ENGINEERING COMPANY, Hubei (CN)

(72) Inventors: Zhichao Dong, Tianjin (CN); Danzhong Liu, Wuhan (CN); Jinfang Hou, Tianjin (CN); Aimin Liu, Tianjin (CN); Binbin Xu, Tianjin (CN)

(73) Assignees: TIANJIN PORT ENGINEERING INSTITUTE CO., LTD. OF CCCC FIRST HARBOR ENGINEERING CO., LTD, Tianjin (CN); CCCC FIRST HARBOR ENGINEERING CO., LTD., Tianjin (CN); TIANJIN PORT ENGINEERING QUALITY TESTING CENTER CO., LTD., Tianjin (CN); CHANGJIANG WUHAN WATERWAY ENGINEERING COMPANY, Wuhan (CN)

( * ) Notice: Subject to any disclaimer, the term of this patent is extended or adjusted under 35 U.S.C. 154(b) by 0 days.

(21) Appl. No.: 18/166,464

(22) Filed: Feb. 8, 2023

(65) Prior Publication Data
US 2023/0184735 A1 Jun. 15, 2023

Related U.S. Application Data

(63) Continuation of application No. PCT/CN2022/085101, filed on Apr. 2, 2022.

(30) Foreign Application Priority Data

Apr. 29, 2021 (CN) .......................... 202110474456.1

(51) Int. Cl.
*G01N 33/18* (2006.01)
*G01M 10/00* (2006.01)
*G01N 11/04* (2006.01)

(52) U.S. Cl.
CPC ............ *G01N 33/18* (2013.01); *G01M 10/00* (2013.01); *G01N 11/04* (2013.01)

(58) Field of Classification Search
CPC .... G01N 33/18; G01N 33/1838; G01N 11/04; G01M 10/00
See application file for complete search history.

(56) References Cited

U.S. PATENT DOCUMENTS 6,494,084 B1 * 12/2002 Roberts .................. G01N 11/00
73/86
6,679,105 B1 1/2004 Jepsen et al.

FOREIGN PATENT DOCUMENTS

CN 102539635 A 7/2012
CN 102539644 A * 7/2012
(Continued)

OTHER PUBLICATIONS

Decision to Grant a Patent in Chinese Application No. 202110474456.1 dated Jan. 26, 2022, 4 pages.
(Continued)

*Primary Examiner* — Michael J Dalbo
(74) *Attorney, Agent, or Firm* — METIS IP LLC (57) ABSTRACT

The disclosure discloses a test method for simulating sediment pollutant release under the effect of river channel erosion, which comprises preparing a test device, presetting a water depth and a flow velocity in a test water tank, and calculating a flow rate in the test water tank; paving the (Continued)

sediment in a sediment storage box, and covering an upper surface of the sediment with a water baffle; adding water into the test water tank until a preset water depth, starting a variable speed motor to drive a flow-making propeller to run to make the flow rate reach the required flow rate and keep the flow velocity constant; after the water flow becomes constant, the water baffle retracting to expose the surface of the sediment; opening sampling ports for layered sampling; measuring water; and respectively measuring concentration variation and vertical distribution features of sediment pollutant under different simulated power conditions.

10 Claims, 6 Drawing Sheets

(56) References Cited

FOREIGN PATENT DOCUMENTS

| CN | 102539644 A | | 7/2012 |
|---|---|---|---|
| CN | 103335817 A | | 10/2013 |
| CN | 103869048 A | | 6/2014 |
| CN | 104075872 A | * | 10/2014 |
| CN | 106840600 A | * | 6/2017 |
| CN | 106840600 A | | 6/2017 |
| CN | 107036785 A | | 8/2017 |
| CN | 207163691 U | | 3/2018 |
| CN | 108645758 A | | 10/2018 |
| CN | 110528454 A | | 12/2019 |
| CN | 111794174 A | * | 10/2020 |
| CN | 113324730 B | | 3/2022 |
| JP | 2003213721 A | | 7/2003 |
| JP | 2014174134 A | | 9/2014 |

OTHER PUBLICATIONS

International Search Report in PCT/CN2022/085101 dated Jun. 8, 2022, 8 pages.

Written Opinion in PCT/CN2022/085101 dated Jun. 8, 2022, 6 pages.

Kuang, Cuiping et al., Impact of Dredging Project on Water Exchange of Qilihai Lagoon Wetland, China Environmental Science, 39(1): 343-350, 2019.

Lisa Richman et al., Monitoring Re-Suspension and Transport of Dioxin Contaminated Sediment to Evaluate the Recovery of a Shallow Urban Creek Post Sediment Remediation, Journal of Environmental Protection, 7: 453-466, 2016.

* cited by examiner

TEST METHODS FOR SIMULATING SEDIMENT POLLUTANT RELEASE UNDER EFFECT OF RIVER CHANNEL EROSION

CROSS-REFERENCE TO RELATED APPLICATIONS

This application is a Continuation of International Application No. PCT/CN2022/085101, filed on Apr. 2, 2022, which claims priority to Chinese Patent Application No. 202110474456.1, filed on Apr. 29, 2021, the entire contents of which are hereby incorporated by reference.

TECHNICAL FIELD

The present disclosure belongs to the technical field of water conservancy engineering, and in particular to a test method for simulating sediment pollutant release under the effect of river channel erosion.

BACKGROUND

With the continuous acceleration of urbanization, a large number of industrial and agricultural wastewater and sewage from human activities are discharged, and industrial and domestic wastes are dumped into rivers and lakes, resulting in increasingly prominent water environment problems such as water eutrophication and heavy metal pollution. The sedimentation and accumulation of pollutants in the sediment of rivers and lakes may move forward and diffuse to the upper water body under the action of self-diffusion and external force, causing obvious "secondary pollution" to the water body, making the endogenous pollution of the sediment more and more serious. Especially, in estuarine areas with complex hydraulic conditions, the endogenous release of contaminated sediment is becoming more and more obvious. For shallow lakes and rivers that are subject to large hydrodynamic disturbances, the sediment pollutants in the water body are prone to resuspension, which has a greater impact on the entire water body and water environment.

Many studies have been carried out on the release features of sediment pollutants. This type of research is mainly based on the method of physical model test. The effects of water disturbance on the release of sediment pollutants are simulated by methods such as swirl, piston, and oscillation, which may not directly and accurately reflect the real water flow conditions.

Therefore, it is desirable to develop a test method for simulating sediment release, which may truly reflect real power conditions of river erosion, and have little influence on sediment disturbance in the flow-making process.

SUMMARY

One or more embodiments of the present disclosure provide a test method for simulating sediment pollutant release under the effect of river channel erosion. The method comprises the following steps. Step 1: preparing a test device. The test device includes a leveling base, a test water tank, a sediment storage mechanism for adjusting a thickness of the sediment, a flow-making mechanism for simulating river channel erosion, and a flowmeter for measuring a flow rate. The test water tank is installed on the leveling base, the test water tank is enclosed by a flow-making section, a test section, and two arc sections. The flow-making section and the test section are arranged in parallel, and two ends of the flow-making section and two ends of the test section are respectively connected with the two arc sections to form an oblong water tank. A concave flow-making groove is arranged in an inner wall of the flow-making section, and a test port is arranged in a middle of a bottom of the test section. A width of the flow-making section is smaller than a width of the test section. A plurality of sampling ports are arranged in an outer wall of the test section, sampling pipes are connected to the sampling ports, and water stop clips are installed on the sampling pipes. A bottom of the leveling base is provided with support feet for adjusting horizontal position of the leveling base. The sediment storage mechanism is installed at bottom of the test water tank, and the sediment storage mechanism includes a sediment storage box, a roller shutter, a water baffle, an adjusting bottom plate, and support rods. The sediment storage box is installed right below the test port, the roller shutter is installed on top of the leveling base, and the roller shutter is located at a left edge of the test port. The water baffle is wound in the roller shutter and driven by the roller shutter, a movable end of the water baffle extends into the test port of the test water tank in an extended state to close the bottom of the test water tank under the driving of the roller shutter, a bottom of the adjusting bottom plate is provided with the support rods, and the adjusting bottom plate is installed in the sediment storage box and position of the adjusting bottom plate in the sediment storage box is fixed through the support rods to adjust the thickness of the sediment in the test. The flow-making mechanism includes a variable speed motor and a flow-making propeller, the flow-making propeller is installed in the flow-making groove, the variable speed motor is installed on the leveling base, and an output shaft of the variable speed motor is connected with a bottom of the flow-making propeller to drive the flow-making propeller to rotate to simulate water flow in the flow-making section; and the flowmeter is installed above the test section. Step 2: presetting a water depth and a flow velocity U in the test water tank according to a test need, and calculating the flow rate Q in the test water tank according to the flow velocity U according to formulas:

$$Q = U \times A \quad (1);$$

$$A = w \times h \quad (2);$$

where A denotes a cross-sectional area of the test water tank, h denotes the water depth in the test water tank, and w denotes the width of the test section. Step 3: presetting a thickness of sediment, paving the sediment in the sediment storage box according to the thickness of the sediment, and adjusting the adjusting bottom plate to make a surface of the sediment flush with the bottom of the test water tank, and then controlling the roller shutter to make the water baffle cover an upper surface of the sediment. Step 4: adding water into the test water tank according to the water depth preset in step 2, starting the variable speed motor to drive the flow-making propeller to run, creating flow in the flow-making groove, then turning on the flowmeter to measure the water flow rate, and then adjusting a speed of the variable speed motor to make the flow rate reach a required flow rate and keep the flow rate constant. Step 5: after the water flow in the test water tank becomes constant, driving the water baffle to retract by the roller shutter to expose the surface of the sediment. Step 6: every 1-2 minutes, opening respectively the sampling ports for layered sampling on water in the test water tank. Step 7: for the water samples obtained in step 6, using a water quality analyzer to measure chemical oxygen demand, a total phosphorus amount, a total nitrogen amount, an ammonia nitrogen amount, and a heavy metal amount in the water respectively. Step 8: adjusting the thickness of the sediment, the water depth or the flow rate in the test water tank according to the test need, repeating the steps 2-7, and measuring the concentration variation and vertical distribution features of the sediment pollutants under different simulated power conditions.

In some embodiments, a length of the flow-making section and a length of the test section are 1.5 m, a width of the flow-making section is 10 cm, a width of the test section is 40 cm, and a width of the arc sections gradually increases from the flow-making section to the test section.

In some embodiments, a height of the test water tank is 1.2 m, and a total length of the test water tank is 1.5 m.

In some embodiments, the test water tank includes an outer wall, an inner wall, and a bottom plate, the test port is arranged on the bottom plate, and a socket is formed in a middle of an edge of one side close to the test port, so that the extended movable end of the water baffle extends into the socket, a size of the test port is 40 cm*40 cm, a thickness of the bottom plate is 5 mm, a thickness of the socket is 5 mm, and a length of the socket is 40 cm.

In some embodiments, the sediment storage box is a cuboid, a length of the sediment storage box is 40 cm, a width of the sediment storage box is 40 cm, a height of the sediment storage box is 60 cm, and a wall thickness of the sediment storage box is 1 cm.

In some embodiments, a plurality of limit holes matched with the support rods are formed in the inner wall of the sediment storage box, and grooves are formed in the bottom of the adjusting bottom plate, the support rods are installed in the grooves and correspondingly installed in the limit holes to adjust the position of the adjusting bottom plate in the sediment storage box.

In some embodiments, eleven sampling ports are arranged at equal intervals from bottom to top, a diameter of each sampling port is 0.8 cm, and a hole spacing of each sampling port is 3 cm, 13 cm, 23 cm, 33 cm, 43 cm, 53 cm, 63 cm, 73 cm, 83 cm, 93 cm, and 103 cm from bottom to top sequentially.

In some embodiments, the leveling base includes a support frame, and a front end and a rear end of the support frame are symmetrically provided with upward protrusions so that front and rear sides of the test water tank are clamped on the support frame.

In some embodiments, the flowmeter is fixedly mounted on the top of the test section using a mounting frame, and the flowmeter is an ultrasonic flowmeter.

In some embodiments, the flow-making propeller is a three-bladed propeller, a height of the flow-making propeller is the same as the height of the test water tank, and the flow-making propeller is driven by the variable speed motor to simulate different power conditions of the river channel in the flow-making section.

BRIEF DESCRIPTION OF THE DRAWINGS

This disclosure will be further described by way of exemplary embodiments, which will be described in detail by means of the accompanying drawings. These embodiments are not limiting, and in these embodiments, the same numbers refer to the same structures, wherein.

DETAILED DESCRIPTION

In order to more clearly illustrate the technical schemes of the embodiments of the present disclosure, the accompanying drawings that need to be used in the description of the embodiments will be briefly introduced below. Obviously, the accompanying drawings in the following description are only some examples or embodiments of the present disclosure. For ordinary technicians skilled in the art, the present disclosure may also be applied to other similar situations according to these drawings without any creative effort. Unless obvious from the locale or otherwise specified, the same reference numbers in the drawings represent the same structure or operation.

It should be understood that "system", "device", "unit" and/or "module" as used herein is a method used to distinguish different components, elements, parts, portions or assemblies at different levels. However, other words may be replaced by other expressions if they serve the same purpose.

As shown in this disclosure and the claims, unless the context clearly indicates an exception, the words "a", "an", "a kind" and/or "the" are not intended to specifically refer to the singular, but may also comprise the plural. In generally, the terms "comprising" and "including" only imply that the clearly identified steps and elements are included, and these steps and elements do not constitute an exclusive list, and the method or equipment may also comprise other steps or elements.

Flowcharts are used in this disclosure to illustrate operations performed by the system according to the embodiments of the present disclosure. It should be understood that the preceding or following operations are not necessarily performed in the exact order. Instead, the various steps may be processed in reverse order or simultaneously. At the same time, other operations may be added to these procedures, or a step or steps may be removed from these procedures.

Figure 1:
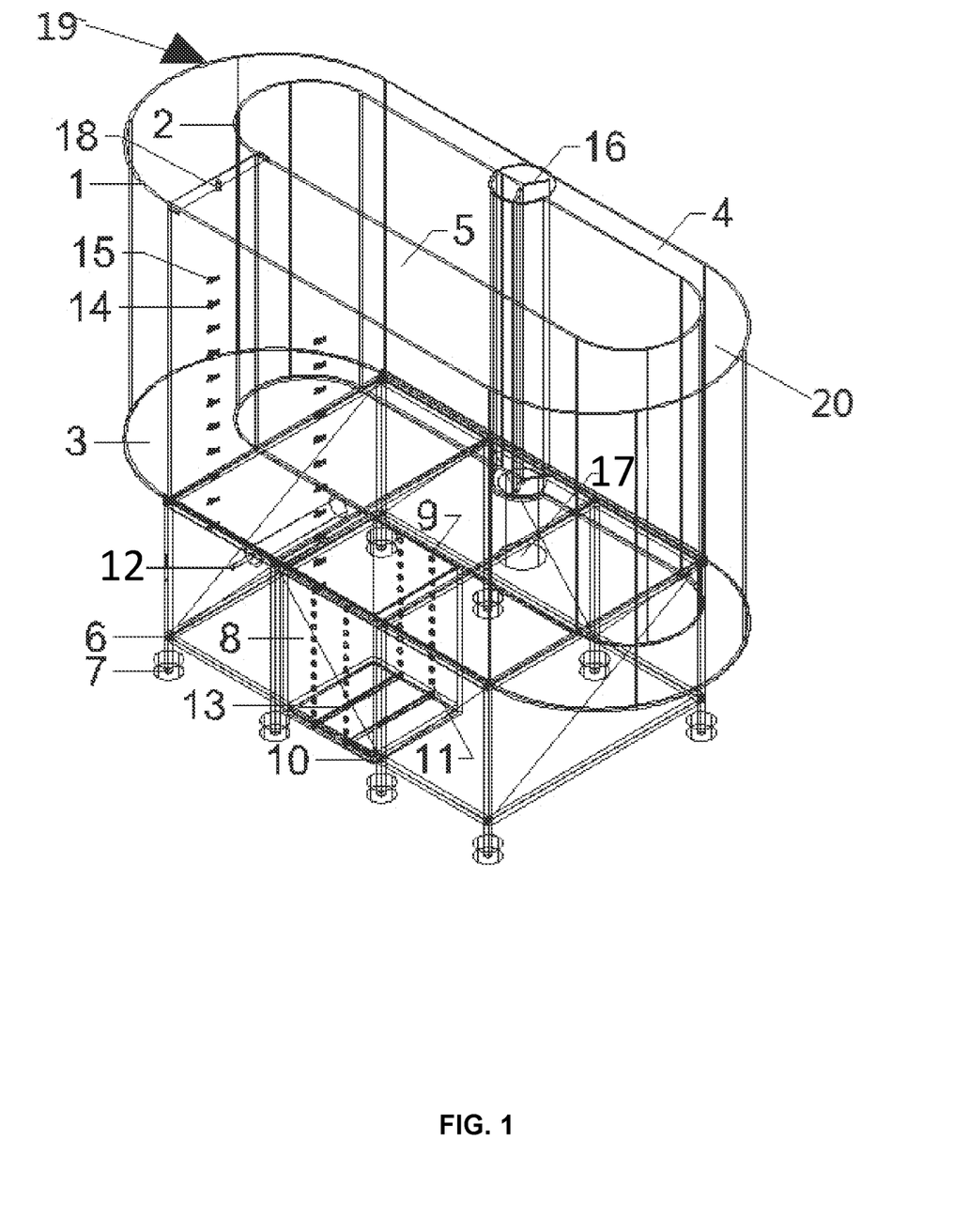
FIG. 1 is a structural schematic diagram of the test device according some embodiments of the present disclosure.
Figure 2:
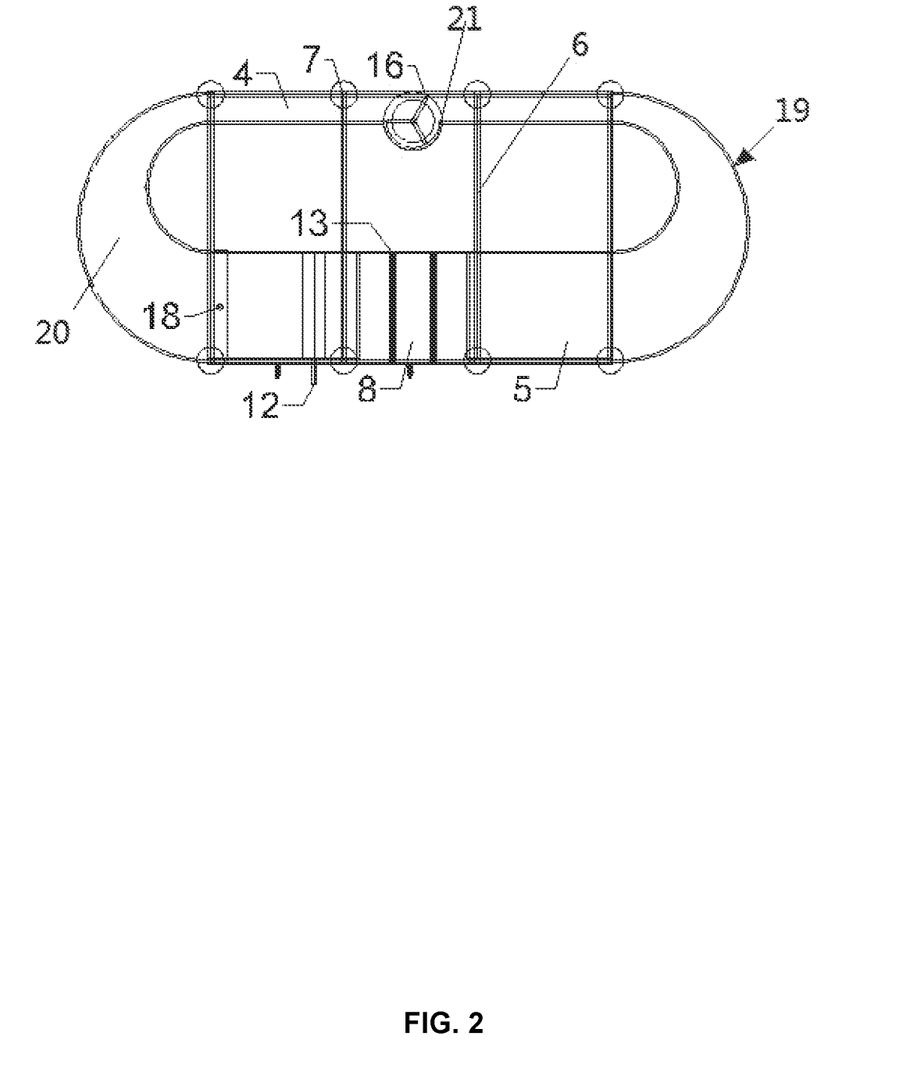
FIG. 2 is a top view of the test device according some embodiments of the present disclosure.

FIG. 1 is a structural schematic diagram of the test device according some embodiments of the present disclosure. FIG. 2 is a top view of the test device according some embodiments of the present disclosure.

As shown in FIG. 1, in some embodiments, the test device for simulating the sediment pollutant release under the effect of river channel erosion comprises: a leveling base 6, a test water tank 19, a sediment storage mechanism, a flow-making mechanism, and a flowmeter 18.

The test water tank 19 may refer to a main device for performing a test. In some embodiments, the test water tank 19 may be installed on the leveling base 6.

As an example only, a height of the test water tank 19 is 1.2 m, and a total length of the test water tank 19 is 1.5 m.

In some embodiments, as shown in FIG. 2, the test water tank 19 may be enclosed by a flow-making section 4, a test section 5 and two arc sections 20. The flow making section 4 may refer to a part used to make the flow of the water. The test section 5 may refer to a part used to perform a sediment pollution release test. The arc sections 20 may refer to parts for connecting the flow-making section 4 and the test section 5. In some embodiments, the flow-making section 4 and the test section 5 may be arranged in parallel, and the two ends of the flow-making section 4 and the two ends of the test section 5 are respectively connected with the two arc sections 20 to form an oblong test water tank 19.

In one specific embodiment, a length of the flow-making section 4 and a length of the test section 5 are 1.5 m, a width of the flow-making section 4 is 10 cm, a width of the test section 5 is 40 cm, and a width of the arc sections gradually increases from the flow-making section to the test section.

In some embodiments, a concave flow-making groove 21 is formed in an inner wall 2 of the flow-making section 4. In some embodiments, the flow-making groove may be used to arrange the flow-making mechanism, and the flow-making mechanism may be used to simulate river channel erosion. In some embodiments, the flow-making mechanism may include a variable speed motor 17 (60 W Leonhard variable speed motor) and a flow-making propeller 16, the flow-making propeller 16 may be installed in the flow-making groove 21, and the variable speed motor 17 may be installed on the leveling base 6. An output shaft of the variable speed motor 17 is connected with a bottom of the flow-making propeller 16 to drive the flow-making propeller 16 to rotate to simulate water flow in the flow-making section 4.

In one specific embodiment, the flow-making propeller 16 may be a three-bladed propeller, a height of the flow-making propeller is the same as the height of the test water tank 19, and the flow-making propeller may be driven by the variable speed motor 17 to simulate different power conditions of the river channel in the flow-making section 4.

In some embodiments, a test port 24 is formed in a middle of a bottom of the test section 5. The test port 24 may be used to release the sediment pollutants. In some embodiments, the width of the flow-making section 4 may be smaller than the width of the test section 5.

In some embodiments, a plurality of sampling ports are formed in an outer wall 1 of the test section 5, sampling pipes 14 are connected to the sampling ports, and water stop clips 15 are installed on the sampling pipes 14.

As an example only, eleven sampling ports are arranged at equal intervals from bottom to top, a diameter of each sampling port is 0.8 cm, and a hole spacing of each sampling port is 3 cm, 13 cm, 23 cm, 33 cm, 43 cm, 53 cm, 63 cm, 73 cm, 83 cm, 93 cm, and 103 cm from bottom to top sequentially.

The flowmeter 18 may be used to measure the flow rate. In some embodiments, the flowmeter may be installed above the test section 5 to measure the flow rate of the test section 5.

In some embodiments, the flowmeter 18 may be fixedly mounted on the top of the test section 5 using a mounting frame. In one specific embodiment, the flowmeter may be an ultrasonic flowmeter 18.

In some embodiments, by performing sampling analysis to the water of different heights, the vertical distribution features of the sediment pollutant release may be studied, and the power conditions of the test water tank may be measured through the flowmeter, thereby effectively reducing the effect of sampling and measurement on the hydrodynamic field.

Figure 4:
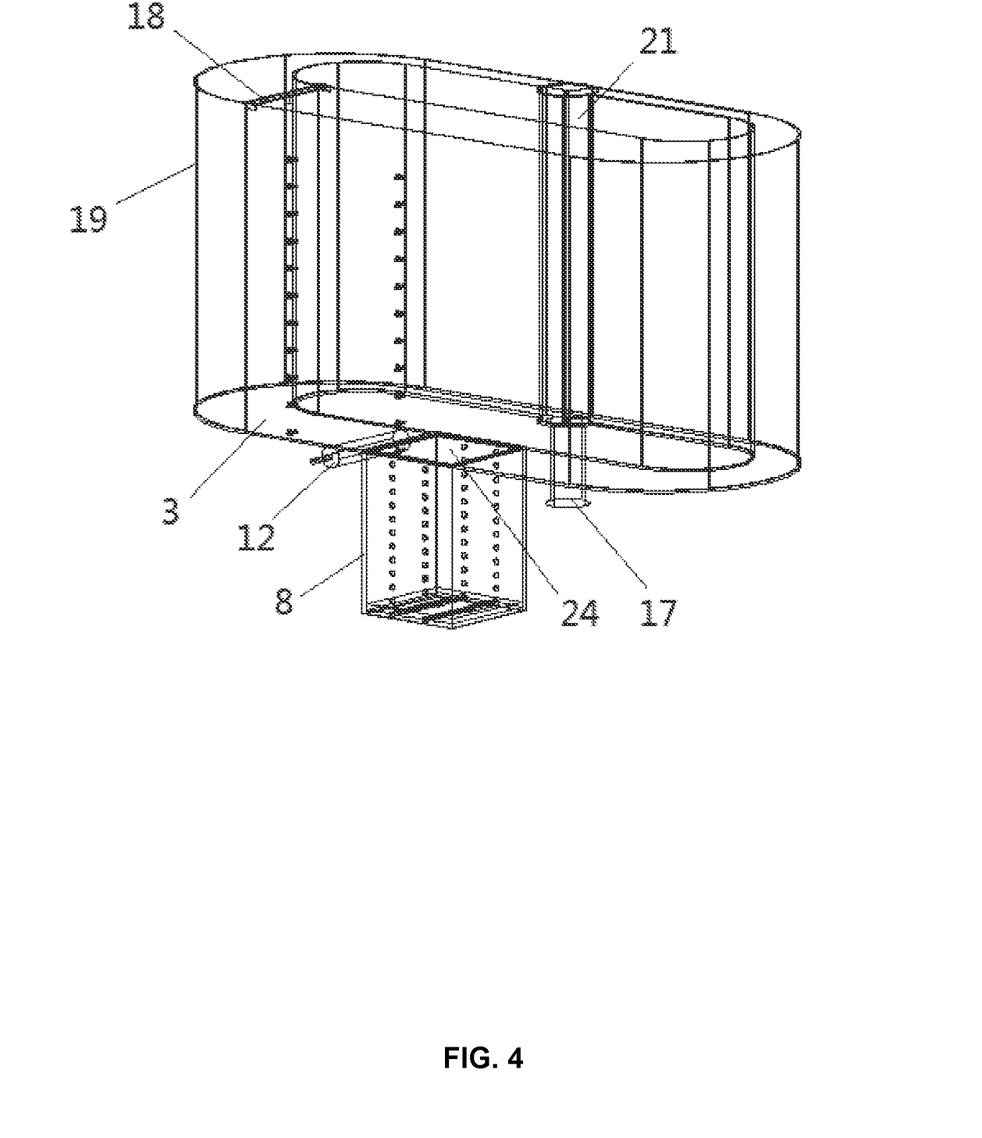
FIG. 4 is a structural schematic diagram of the test water tank according some embodiments of the present disclosure.

FIG. 4 is a structural schematic diagram of the test water tank according some embodiments of the present disclosure.

The sediment storage mechanism may be used to adjust the thickness of the sediment. In some embodiments, the sediment storage mechanism may be installed at the bottom of the test water tank 19, and the sediment storage mechanism may include a sediment storage box 8, a roller shutter 12, a water baffle 9, an adjusting bottom plate 10 and support rods 13, as shown in FIG. 4.

The sediment storage box 8 is used to store the sediment. In one specific embodiment, the sediment storage box 8 may be a cuboid, a length of the sediment storage box 8 is 40 cm, a width of the sediment storage box 8 is 40 cm, a height of the sediment storage box 8 is 60 cm, and a wall thickness of the sediment storage box 8 is 1 cm.

In some embodiments, the sediment storage box 8 may be located right below the test port 24, for example, the top of the sediment storage box 8 may be fixedly installed right below the test port 24. In some embodiments, the bottom of the adjusting bottom plate 10 is provided with the support rods 13. The adjusting bottom plate 10 is installed in the sediment storage box 8 and the position of the adjusting bottom plate 10 in the sediment storage box 8 is fixed through the support rods 13 to adjust the thickness of the sediment in the test.

In some embodiments, a plurality of limit holes 11 matched with the support rods 13 are formed in the inner wall 2 of the sediment storage box 8, grooves are formed in the bottom of the adjusting bottom plate 10, and the support rods are installed in the grooves and correspondingly installed in the limit holes 11 to adjust the position of the adjusting bottom plate 10 in the sediment storage box 8.

In one specific embodiment, the limit holes 11 are symmetrically arranged in two columns on the inner wall of the sediment storage box 8, a diameter of each limit hole 11 is 20 mm, a spacing between the two columns of limit holes is 150 mm, and a spacing between the adjacent upper and lower limit holes of each column is 50 mm.

The roller shutter 12 is used to drive the water baffle 9 to move to close or open the test port 24. In some embodiments, the roller shutter 12 may be installed on the top of the leveling base 6, and the roller shutter 12 may be located at any edge (e.g., a left edge according to FIG. 4) of the test port 24. The water baffle 9 is wound in the roller shutter 12 and driven by the roller shutter 12. The movable end of the water baffle 9 extends into the test port 24 of the test water tank 19 in the extended state to close the bottom of the test water tank 19 under the driving of the roller shutter 12.

In some embodiments, the test water tank 19 may include the outer wall 1, the inner wall 2, and a bottom plate 3, the test port 24 may be arranged on the bottom plate 3, and a socket is formed in the middle of the edge of one side close to the test port 24, so that the extended movable end of the water baffle 9 extends into the socket. In one specific embodiment, the size of the test port 24 is 40 cm*40 cm, the thickness of the bottom plate 3 is 5 mm, the thickness of the socket is 5 mm, and the length of the socket is 40 cm.

In some embodiments, the sediment storage mechanism may be used to set different thicknesses of sediment to study the influence of different sediment thicknesses on the features of pollutants, and the influence of an initial flow-making process on the sediment disturbance may be reduced based on the setting of the water baffle.

Figure 3:
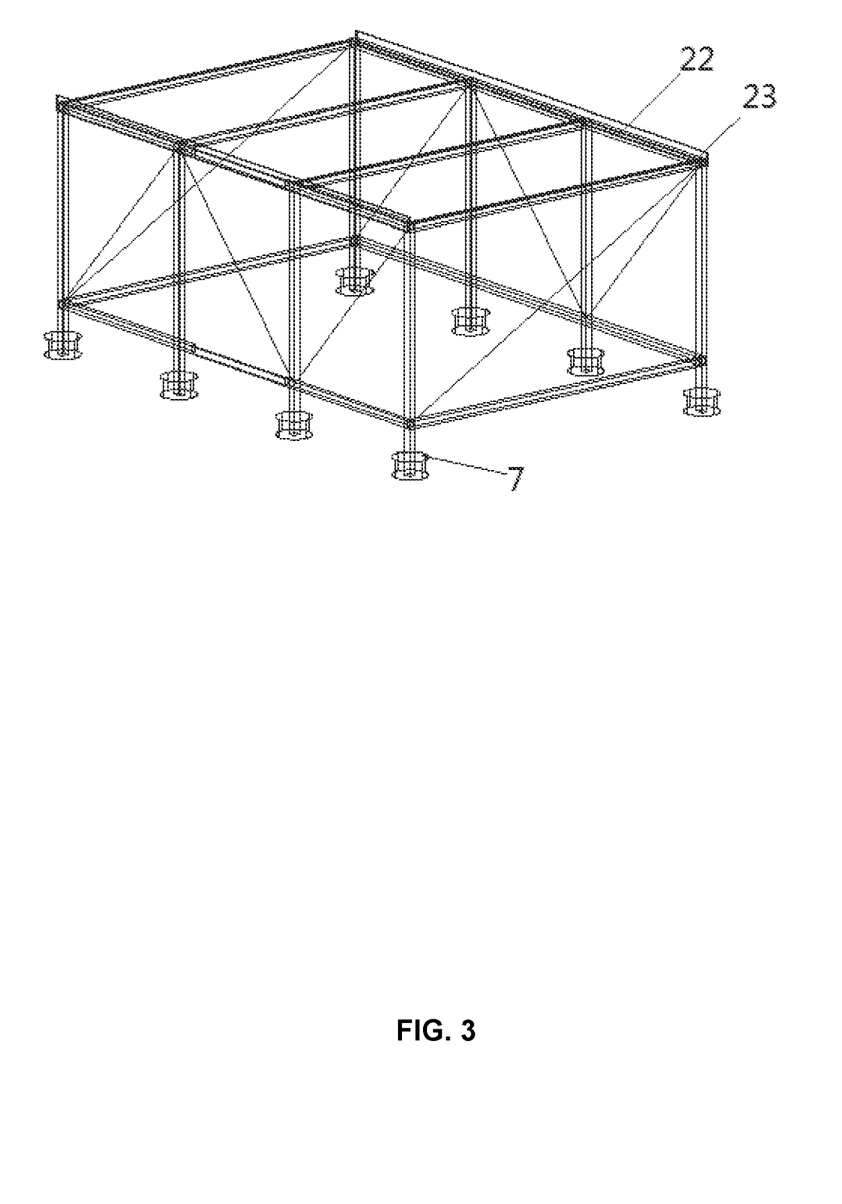
FIG. 3 is a structural schematic diagram of the leveling base according some embodiments of the present disclosure.

FIG. 3 is a structural schematic diagram of the leveling base according some embodiments of the present disclosure.

The leveling base 6 may be used to support the test device and used to adjust the test device to a horizontal position. In some embodiments, the bottom of the leveling base 6 is provided with support feet 7 for adjusting the horizontal position of the leveling base 6.

As shown in FIG. 3, in some embodiments, the leveling base may include a support frame 22, and front and rear ends of the support frame 22 are symmetrically provided with upward protrusions 23 so that the front and rear sides of the test water tank 19 are clamped on the support frame 22. In some embodiments, the support feet 7 may be installed on the bottom of the support frame 22, and the support feet 7 have the function of rotating to fine-tune the height, and the test water tank 19 may be in a horizontal state by adjusting the height of the support feet 7.

In some embodiments, the test method for simulating the sediment pollutant release under the effect of river channel erosion may be performed through the test device, comprising the following steps.

Step 1: preparing the test device.

Step 2: presetting a water depth and a flow velocity U in the test water tank according to the test need, and calculating a flow rate Q in the test water tank according to the flow velocity according to the following formulas:

$$Q = U \times A \quad (1);$$

$$A = w \times h \quad (2);$$

where A denotes a cross-sectional area of the test water tank, h denotes the water depth in the test water tank, and w denotes the width of the test section.

Step 3: presetting a thickness of the sediment, paving the sediment in the sediment storage box according to the thickness of the sediment, and adjusting the adjusting bottom plate to make a surface of the sediment flush with the bottom of the test water tank, and then controlling the roller shutter to make the water baffle cover an upper surface of the sediment.

Step 4: adding water into the test water tank according to the water depth preset in step 2, starting the variable speed motor to drive the flow-making propeller to run, creating flow in the flow-making groove, then turning on the flowmeter to measure the water flow rate, and then adjusting a speed of the variable speed motor to make the flow rate reach a required flow rate and keep the flow rate constant.

Step 5: after the water flow in the test water tank becomes constant, driving the water baffle to retract by the roller shutter to expose the surface of the sediment.

Step 6: every 1-2 minutes, opening respectively the sampling ports for layered sampling on water in the test water tank.

Step 7: for the water samples obtained in step 6, using a water quality analyzer to measure chemical oxygen demand, a total phosphorus amount, a total nitrogen amount, an ammonia nitrogen amount, and a heavy metal amount in the water respectively.

step 8: adjusting the thickness of the sediment, the water depth or the flow rate in the test water tank according to the test need, repeating the steps 2-7, and measuring the concentration variation and vertical distribution features of the sediment pollutants under different simulated power conditions.

In some embodiments, the test method for simulating the sediment pollutant release under the effect of river channel erosion may be used to study the cumulative effect of the sediment pollutant release, generalize the impact of pollutant diffusion, and prevent secondary pollution of pollutants to the test environment, and the test method has high working efficiency, reducing the manpower and time required for test layout and test environment cleaning.

Taking the simulation of the Qilihai Lagoon Wetland Changli in National Nature Reserve, Hebei Province as an example, the test method for simulating the sediment pollutant release under the effect of river channel erosion is further described. The rivers entering the Qilihai Lagoon are all seasonal rivers, difference of annual flow is large, the monthly average runoff changes within a range of 0-2 m$^3$/s, the average water depth of the river is 0.5 m, and the average flow velocity of the river is within a range of 0-0.1 m/s. The test device of the embodiments is used to study the influence mechanism of the sediment release the in the rivers entering into the Qilihai Lagoon, which may provide a theoretical basis for engineering environmental assessment and environmental management.

The application of the test method for simulating the sediment pollutant release under the effect of river channel erosion is studied on the influence of the thickness of the sediment on the release of the sediment, comprising the following steps.

(1) According to the river and lake conditions of the Qilihai Lagoon, presetting a river velocity as 0.1 m/s, and a river depth as 0.5 m, and calculating the flow rate in the test water tank 19 to be 0.02 m$^3$/s according to the preset river velocity and river depth.

(2) According to the thickness of the sediment, paving the sediment in the sediment storage box 8, the thickness of the sediment being 0.1 m, and adjusting the adjusting bottom plate 10 to make the surface of the sediment flush with the bottom of the test water tank 19, and then controlling the roller shutter 12 to make the water baffle 9 cover the upper surface of the sediment.

(3) Adding water to the test water tank 19 until a water depth of 0.5 m, starting the variable speed motor 17 to drive the flow-making propeller to run, creating flow in the flow-making groove, then turning on the flowmeter 18 to measure the water flow rate, and then adjusting the speed of the variable speed motor 17 to make the reading of the flowmeter reach 0.02 m$^3$/s and keep the speed of the variable speed motor 17 constant.

(4) After the water flow in the test water tank 19 becomes constant, the roller shutter 12 driving the water baffle 9 to retract to expose the surface of the sediment to be in contact with water.

(5) Every 2 minutes, opening all the sampling ports below the water depth of 0.5 m, opening the water stop clips on the sampling pipes, and layered sampling 50 mL water in the test water tank, and then closing the water stop clips after sampling.

(6) For the water samples obtained in step 5, using a water quality analyzer to measure chemical oxygen demand, a total phosphorus amount, a total nitrogen amount, an ammonia nitrogen amount and a heavy metal amount in the water respectively.

(7) Adjusting the thickness of the sediment to 0.2 m, 0.3 m, 0.4 m and 0.5 m, and repeating the above steps (1)-(6) to measure the influence of river channel erosion on the release of the pollutants from sediment with different thicknesses under the same power conditions.

(8) After the measurement is completed, cleaning the test water tank 19 and the sediment storage box 8 to complete the simulation test.

The application of the test method for simulating the sediment pollutant release under the effect of river channel erosion is studied on the influence of the variation of the power conditions on the release of the sediment, comprising the following steps.

(1) According to the river and lake conditions of the Qilihai Lagoon, presetting a river depth as 0.5 m, a thickness of sediment as 0.5 m, and a river velocity as 0.02 m/s, and calculating the flow rate in the test water tank 19 to be 0.004 m$^3$/s according to the river velocity.

(2) According to the thickness of the sediment, paving the sediment with the thickness of the sediment of 0.5 m in the sediment storage box 8, and adjusting the adjusting bottom plate 10 to make the surface of the sediment flush with the bottom of the test water tank 19, and then controlling the roller shutter 12 to make the water baffle 9 cover the upper surface of the sediment.

(3) Adding water to the test water tank 19 until a water depth of 0.5 m, starting the variable speed motor 17 to drive the flow-making propeller to run, creating flow in the flow-making groove, and then adjusting the speed of the variable speed motor 17 to make the reading of the flowmeter reach 0.004 $m^3/s$, and keep the speed of the variable speed motor 17 constant.

(4) After the water flow in the test water tank 19 becomes constant, the roller shutter 12 driving the water baffle 9 to retract to expose the surface of the sediment to be in contact with water.

(5) Every 2 minutes, opening all the sampling ports below the water depth of 0.5 m, opening the water stop clips on the sampling pipes, and layered sampling 50 mL water in the test water tank, and then closing the water stop clips after sampling.

(6) For the water samples obtained in step (5), using the water quality analyzer to measure chemical oxygen demand, a total phosphorus amount, a total nitrogen amount, an ammonia nitrogen amount, and a heavy metal amount in the water respectively.

(7) Making the reading of the flowmeter to reach 0.008 $m^3/s$, 0.012 $m^3/s$, 0.016 $m^3/s$ and 0.020 $m^3/s$ by adjusting the speed of the variable speed motor, and repeating the above steps (1)-(6) to measure the influence of different flow velocity on the sediment pollutant release under the conditions of the same thickness of the sediment and water depth.

(8) After the measurement is completed, cleaning the test water tank 19 and the sediment storage box 8 to complete the simulation test.

In actual situations, the water flow velocity of rivers and lakes at different layers (depth) may be different. In addition, the water flow velocity may also be affected by factors such as wind power, rainfall, river depths, terrain and topography. In some embodiments, based on river environmental data, including but not limited to wind power, rainfall, river depth, terrain and topography, etc., the water flow velocity in the corresponding environment may be determined to simulate a more realistic test environment. Further, since the water flow velocity of different layers (depth) is different, the test environment of each layer may be simulated separately. In some embodiments, the test device may include a controller, and the controller may be used to control the rotation velocity of the variable speed motor, etc., to control the water flow velocity.

In some embodiments, the data may be collected based on the actual environment of rivers and lakes to obtain the water flow velocity in the corresponding environment for simulation of the test environment. In some embodiments, a model may be used to predict the water flow velocity in the corresponding environment based on the environmental data of rivers and lakes.

Figure 5:
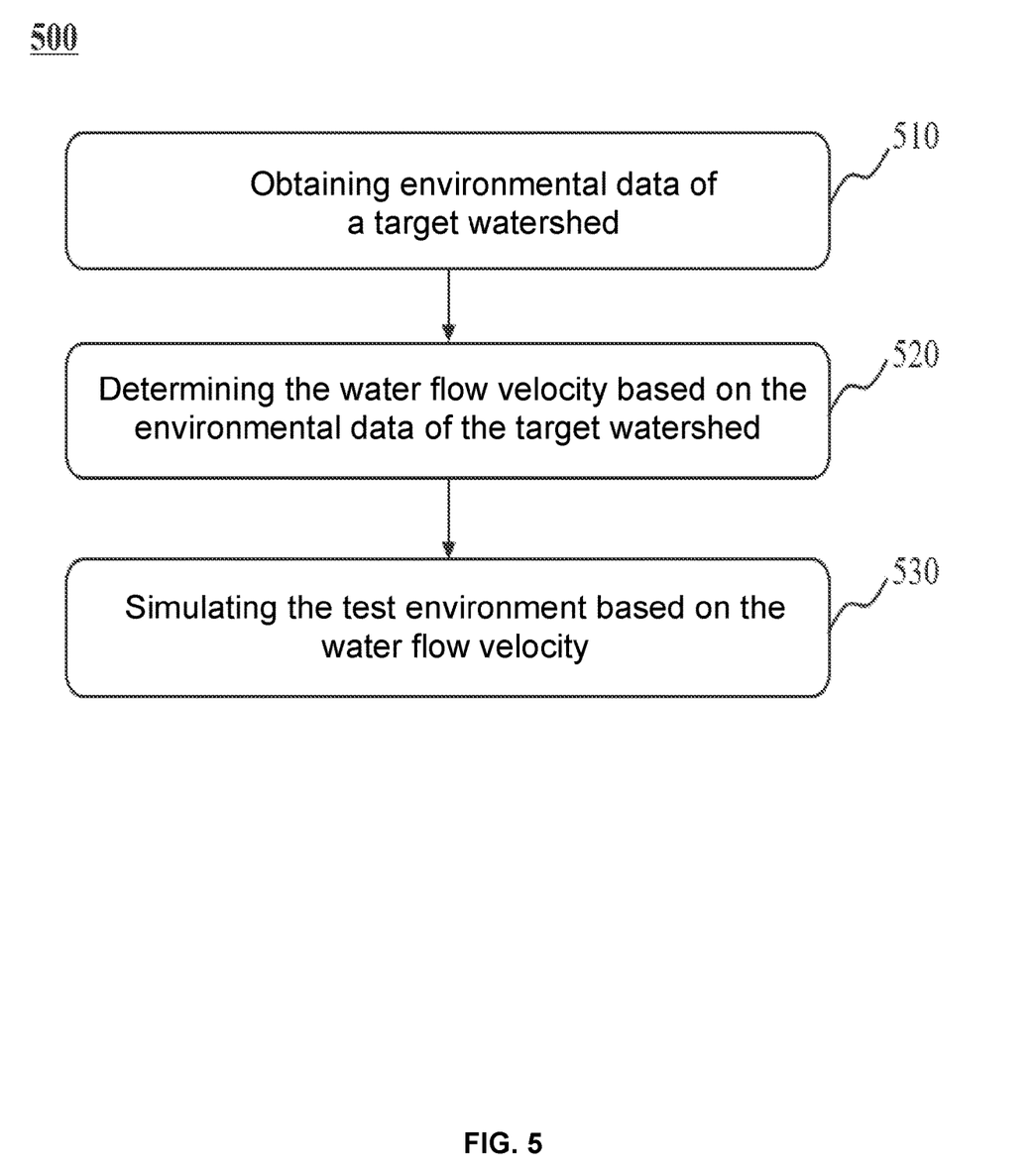
FIG. 5 is a flowchart of the test method according some embodiments of the present disclosure.

FIG. 5 is a flowchart of the test method according some embodiments of the present disclosure. In some embodiments, this process may be performed by a controller. As shown in FIG. 5, the process 500 may comprise the following steps.

Step 510, obtaining environmental data of a target watershed.

The target watershed refers to an area through which the river that needs to perform the simulation test flows. The environmental data may refer to data information related to river status in the target watershed, such as wind power, rainfall, river depth sequences, terrain and topography, sediment volume, or the like. The terrain and topography may comprise terrain types, such as plains, basins, plateaus, etc., and may also comprise topographic drops of the river, etc.

The environmental data of the target watershed may be obtained by setting relevant detection devices in the watershed. For example, wind detection devices, rainfall detection devices, river depth detection devices, sediment volume detection devices, etc. may be installed at a plurality of locations in the target watershed. If the short-term environmental changes in the target watershed are small, the environmental data of the target watershed may also be obtained directly based on historical detection data, without on-site collection, saving manpower and material resources.

Step 520, determining the water flow velocity based on the environmental data of the target watershed.

In some embodiments, the water flow velocity may be determined in various feasible ways, for example, the water flow velocity may be determined through flowmeter detection, or the historical detection data, or the like. In some embodiments, due to the environmental influence of the target watershed, direct detection conditions are limited, it may be difficult to obtain complete data, and the detection process requires a lot of manpower and material resources. Data analysis and other methods may be used to analyze the environmental data of the target watershed to determine the water flow velocity. In some embodiments, the water flow velocity of the target watershed may be predicted through a flow velocity prediction model based on the environmental data of the target watershed. In some embodiments, the flow velocity prediction model may be a machine learning model.

Figure 6:
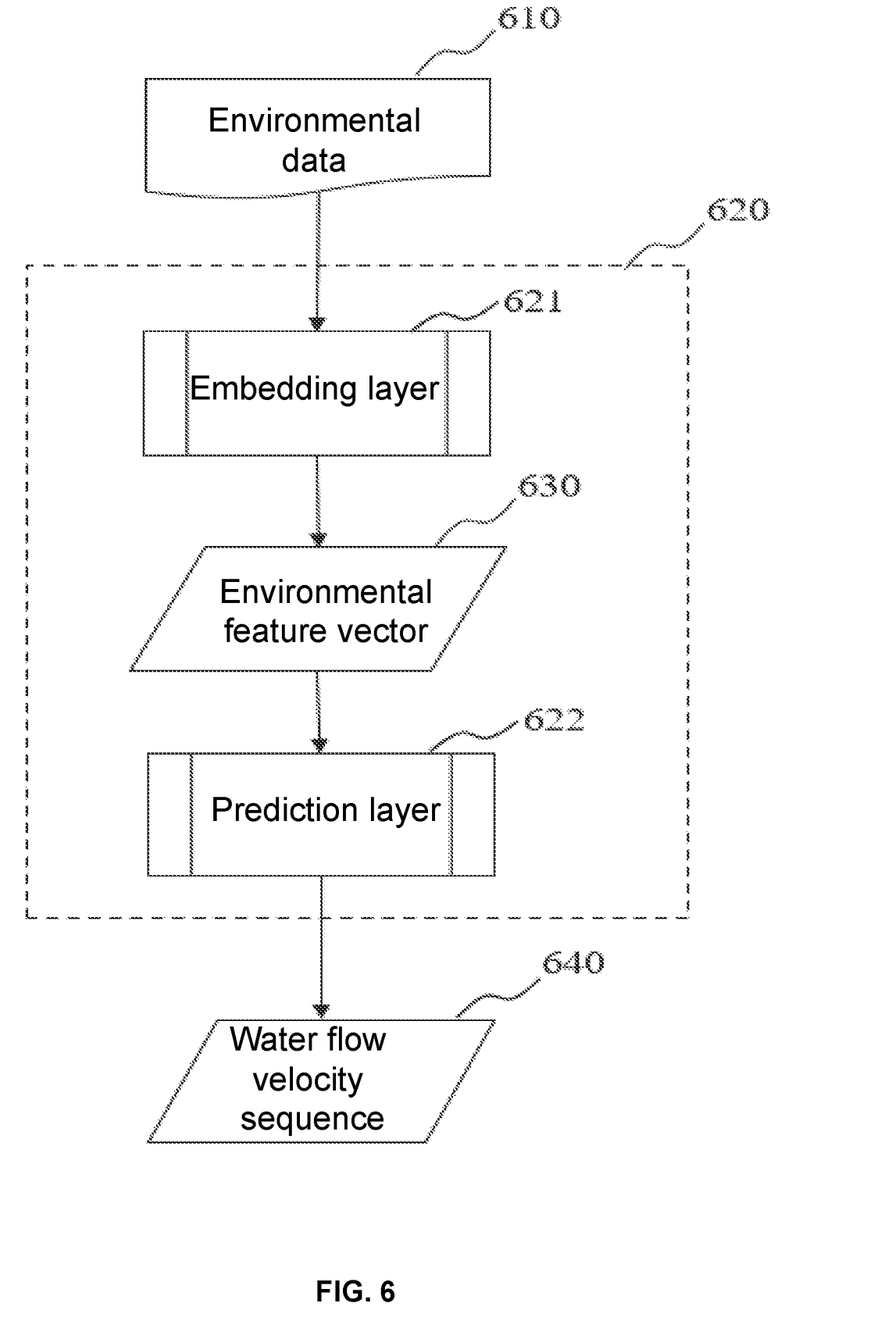
FIG. 6 is a model diagram of a flow velocity prediction model according some embodiments of the present disclosure.

FIG. 6 is a model diagram of a flow velocity prediction model according some embodiments of the present disclosure.

In some embodiments, as shown in FIG. 6, the flow velocity prediction model 620 may comprise an embedding layer 621 and a prediction layer 622. In some embodiments, the embedding layer 621 and the prediction layer 622 may be models derived from a convolutional neural network or a deep neural network or a combination thereof, or the like.

In some embodiments, an input of the embedding layer 621 may comprise the environmental data 610, and an output of the embedding layer 621 may comprise an environmental feature vector 630; an input of the prediction layer 622 may comprise the environmental feature vector 630, and an output of the prediction layer 622 may comprise a water flow velocity sequence 640. The environmental feature vector 630 may be feature data in the form of a vector obtained based on the environmental data 610, and the water flow velocity sequence may be a data sequence used to represent the water flow velocity at a plurality of different depths. In some embodiments, the environmental data 610 may comprise wind power, rainfall, river depth sequences (representing a plurality of river depths), terrain and topography, and sediment volume of the target watershed; the terrain and topography may comprise terrain types (e.g., plains, basins, plateaus) etc.), and topographic drops of the river.

The trained flow velocity prediction model 620 is obtained based on a large amount of extensive data, and the water flow velocity is determined based on the flow velocity prediction model 620, which has high efficiency and certain accuracy, and effectively saves manpower and material resources.

In some embodiments, the flow velocity prediction model 620 may be obtained through separate training or joint training. For example, the embedding layer 621 and the prediction layer 622 may be obtained through joint training, and then the flow velocity prediction model 620 may be obtained. The output of the embedding layer 621 may be used as the input of the prediction layer 622.

For example, sample data is inputted into an initial embedding layer, i.e., a plurality of sets of sample monitoring data of the sample watershed (including wind power, rainfall, sediment amount), and the sample depth data and the sample terrain and topographic data of the sample watershed. The monitoring data may be data of a time period (such as one year) of historical monitoring, the sample environmental feature vector outputted by the initial embedding layer is obtained, and the sample environmental feature vector is inputted into an initial prediction layer to obtain the sample water flow velocity sequence outputted by the initial prediction layer. A loss function is constructed by using the monitored sample water flow velocity of the river at different depth corresponding to each set of sample monitoring data and output results of the initial prediction layer and the parameters of the initial embedding layer and the initial prediction layer are updated based on the loss function until the trained embedding layer and the trained prediction layer are obtained.

Step 530, simulating the test environment based on the water flow velocity.

In some embodiments, the plurality of sampling ports of the test device may be set based on the predicted water flow velocity sequence, that is, the sampling ports may be set at different depth corresponding to the water flow velocity sequence. In some embodiments, a plurality of flow-making mechanisms may be arranged, each layer may be provided with one corresponding flow-making mechanism, and each flow-making mechanism may correspondingly control the water flow velocity at a certain depth. In some embodiments, the water depth of the target watershed is shallow (e.g., less than 2 meters), and the depth corresponding to each layer of flow-making mechanism may completely correspond to the depth of the target watershed. In other embodiments, the water depth of the target watershed is relatively deep, and the depth corresponding to each layer of flow-making mechanism may correspond to the depth of the target watershed in a certain proportion. In order to keep the corresponding proportion, the width of the flow-making section of the test device may be set correspondingly, for example, it may be set wider to keep the cross-sectional area proportion appropriate.

In some embodiments, the rotation speed corresponding to the variable speed motor of each flow-making mechanism may be determined based on the predicted water flow velocity sequence, so as to control the water flow velocity of each layer. By simultaneously starting the plurality of layers of variable speed motors to run at the same time, the plurality of layers may make flow at the same time, so that the real power conditions of the river may be simulated.

In some embodiments, model prediction is used to determine the water flow velocity of each layer based on the test device including the plurality of layers of flow-making mechanisms, it may realize that the water flow velocity of each layer of the test device is as close as possible to the water flow velocity distribution of the actual river and lake, the test environment closer to the actual environment may be obtained through simulation, and the test results are highly accurate.

The basic concept has been described above. Obviously, for technicians skilled in the art, the above detailed disclosure is only an example, and does not constitute a limitation to the specification. Although not explicitly described herein, various modifications, improvements, and corrections to this disclosure may occur to technicians skilled in the art. Such modifications, improvements, and corrections are suggested in this disclosure, so such modifications, improvements, and corrections still belong to the spirit and scope of the exemplary embodiments of this disclosure.

Meanwhile, the present disclosure uses specific words to describe embodiments of the present disclosure. Examples such as "one embodiment," "an embodiment," and/or "some embodiments" mean a certain feature, structure, or characteristic associated with at least one embodiment of this disclosure. Therefore, it should be emphasized and noted that two or more references to "an embodiment" or "one embodiment" or "an alternative embodiment" in various places in this disclosure are not necessarily referring to the same embodiment. Furthermore, certain features, structures or features of the one or more embodiments of this disclosure may be combined as appropriate.

In addition, unless explicitly stated in the claims, the order of processing elements and sequences described in this disclosure, the use of numbers and letters, or the use of other names are not intended to limit the order of the procedures and methods of this disclosure. While the foregoing disclosure discusses some embodiments of the invention by way of various examples that are presently believed to be useful, it is to be understood that such details are for purposes of illustration only and that the appended claims are not limited to the disclosed embodiments, instead, the claims are intended to cover all modifications and equivalent combinations that fall within the spirit and scope of the embodiments of this disclosure. For example, although the system components described above may be implemented by hardware devices, they may also be implemented by software-only solutions, such as installing the described systems on existing servers or mobile devices.

Similarly, it should be noted that, in order to simplify the expressions disclosed in this disclosure to help the understanding of one or more embodiments of the disclosure, in the foregoing description of the embodiments of this disclosure, various features are sometimes merged into one embodiment, drawing or description thereof. However, this method of disclosure does not imply that the subject matter of the description requires more features than are recited in the claims. Indeed, claimed subject matter may lie in less than all features of a single foregoing disclosed embodiment.

In some embodiments, numbers describing the quantities of components and attributes are used, it should be understood that such numbers used for the description of the embodiments, in some examples, use the modifiers "about", "approximately" or "substantially" to retouch. Unless stated otherwise, "about", "approximately" or "substantially" means that a variation of ±20% is allowed for the stated number. Accordingly, in some embodiments, the numerical parameters set forth in the disclosure and claims are approximations that may vary depending upon the desired features of individual embodiments. In some embodiments, the numerical parameters should consider the specified significant digits and use a general digit retention method. Notwithstanding that the numerical fields and parameters used in some embodiments of this disclosure to confirm the breadth of their ranges are approximations, in specific embodiments such numerical values are set as precisely as practicable.

For each patent, patent application, patent application publication and other material, such as an article, a book, a specification, a publication, a document, etc., the entire contents of which are hereby incorporated into this disclosure by reference. Application history documents that are inconsistent with or conflict with the contents of this disclosure are excluded, as are documents (currently or hereafter appended to this disclosure) limiting the broadest scope of the claims of this disclosure. It should be noted that, if there is any inconsistency or conflict between the descriptions, definitions and/or use of terms in the accompanying materials of this disclosure and the contents of this disclosure, the descriptions, definitions and/or use of terms in this disclosure shall prevail.

Finally, it should be understood that the embodiments described in this disclosure are only used to illustrate the principles of the embodiments of this disclosure. Other variations are also possible within the scope of this disclosure. Accordingly, by way of example and not limitation, alternative configurations of the embodiments of this disclosure may be considered consistent with the instructions of this disclosure. Correspondingly, the embodiments of this disclosure are not limited to the embodiments expressly introduced and described in this disclosure.

What is claimed is:

1. A test method for simulating sediment pollutant release under effect of river channel erosion, comprising:

Step 1: preparing a test device, wherein the test device comprises a leveling base, a test water tank, a sediment storage mechanism for adjusting a thickness of the sediment, a flow-making mechanism for simulating river channel erosion, and a flowmeter for measuring an actual water flow rate;

the test water tank is installed on the leveling base, the test water tank is enclosed by a flow-making section, a test section, and two arc sections, the flow-making section and the test section are arranged in parallel, and two ends of the flow-making section and two ends of the test section are respectively connected with the two arc sections to form an oblong water tank, a concave flow-making groove is arranged in an inner wall of the flow-making section, and a test port is arranged in a middle of a bottom of the test section, a width of the flow-making section is smaller than a width of the test section, a plurality of sampling ports are arranged in an outer wall of the test section, sampling pipes are connected to the sampling ports, and water stop clips are installed on the sampling pipes;

a bottom of the leveling base is provided with support feet for adjusting horizontal position of the leveling base;

the sediment storage mechanism is installed at a bottom of the test water tank, and the sediment storage mechanism includes a sediment storage box, a roller shutter, a water baffle, an adjusting bottom plate, and support rods, the sediment storage box is installed right below the test port, the roller shutter is installed on top of the leveling base, and the roller shutter is located at a left edge of the test port, the water baffle is wound in the roller shutter and driven by the roller shutter, a movable end of the water baffle extends into the test port of the test water tank in an extended state to close the bottom of the test water tank under the driving of the roller shutter, a bottom of the adjusting bottom plate is provided with the support rods, the adjusting bottom plate is installed in the sediment storage box and position of the adjusting bottom plate in the sediment storage box is fixed through the support rods to adjust the thickness of the sediment in the test;

the flow-making mechanism includes a variable speed motor and a flow-making propeller, the flow-making propeller is installed in the flow-making groove, the variable speed motor is installed on the leveling base, and an output shaft of the variable speed motor is connected with a bottom of the flow-making propeller to drive the flow-making propeller to rotate to simulate water flow in the flow-making section; and the flowmeter is installed above the test section;

Step 2: presetting a water depth and a flow velocity U in the test water tank according to a test need, and calculating a required water flow rate Q in the test water tank according to the flow velocity U according to formulas:

$$Q = U \times A \qquad (1);$$

$$A = w \times h \qquad (2);$$

where A denotes a cross-sectional area of the test water tank, h denotes the water depth in the test water tank, and w denotes the width of the test section;

Step 3: presetting a thickness of sediment, paving the sediment in the sediment storage box according to the thickness of the sediment, and adjusting the adjusting bottom plate to make a surface of the sediment flush with the bottom of the test water tank, and then controlling the roller shutter to make the water baffle cover an upper surface of the sediment;

Step 4: adding water into the test water tank according to the water depth preset in step 2, starting the variable speed motor to drive the flow-making propeller to run, creating flow in the flow-making groove, then turning on the flowmeter to measure the actual water flow rate, and then adjusting a speed of the variable speed motor to make the actual water flow rate reach the required flow rate and keep the actual water flow rate constant;

Step 5: after the actual water flow in the test water tank becomes constant, driving the water baffle to retract by the roller shutter to expose the surface of the sediment;

Step 6: every 1-2 minutes, opening respectively the sampling ports for layered sampling on water in the test water tank;

Step 7: for the water samples obtained in step 6, using a water quality analyzer to measure chemical oxygen demand, a total phosphorus amount, a total nitrogen amount, an ammonia nitrogen amount, and a heavy metal amount in the water respectively; and Step 8: adjusting the thickness of the sediment, the water depth, or the flow rate in the test water tank according to a test need, repeating steps 2-7, and measuring a concentration variation and a vertical distribution feature of sediment pollutant under different simulated power conditions.

2. The test method of claim 1, wherein a length of the flow-making section and a length of the test section are 1.5 m, a width of the flow-making section is 10 cm, a width of the test section is 40 cm, and a width of the arc sections gradually increases from the flow-making section to the test section.

3. The test method of claim 2, wherein a height of the test water tank is 1.2 m, and a total length of the test water tank is 1.5 m.

4. The test method of claim 3, wherein the test water tank includes an outer wall, an inner wall, and a bottom plate, the test port is arranged on the bottom plate, and a socket is formed in middle of an edge of one side close to the test port, so that the extended movable end of the water baffle extends into the socket, a size of the test port is 40 cm*40 cm, a thickness of the bottom plate is 5 mm, a thickness of the socket is 5 mm, and a length of the socket is 40 cm.

5. The test method of claim 4, wherein the sediment storage box is a cuboid, a length of the sediment storage box is 40 cm, a width of the sediment storage box is 40 cm, a height of the sediment storage box is 60 cm, and a wall thickness of the sediment storage box is 1 cm.

6. The test method of claim 5, wherein a plurality of limit holes matched with the support rods are formed in the inner wall of the sediment storage box, and grooves are formed in the bottom of the adjusting bottom plate, the support rods are installed in the grooves and correspondingly installed in the limit holes to adjust the position of the adjusting bottom plate in the sediment storage box.

7. The test method of claim 6, wherein eleven sampling ports are arranged at equal intervals from bottom to top, a diameter of each sampling port is 0.8 cm, and a hole spacing of each sampling port is 3 cm, 13 cm, 23 cm, 33 cm, 43 cm, 53 cm, 63 cm, 73 cm, 83 cm, 93 cm, and 103 cm from bottom to top sequentially.

8. The test method of claim 7, wherein the leveling base includes a support frame, and a front end and a rear end of the support frame are symmetrically provided with upward protrusions so that front and rear sides of the test water tank are clamped on the support frame.

9. The test method of claim 8, wherein the flowmeter is fixedly mounted on a top of the test section using a mounting frame, and the flowmeter is an ultrasonic flowmeter.

10. The test method of claim 9, wherein the flow-making propeller is a three-bladed propeller, a height of the flow-making propeller is the same as the height of the test water tank, and the flow-making propeller is driven by the variable speed motor to simulate different power conditions of the river channel in the flow-making section.

\* \* \* \* \*